United States Patent
Konishi et al.

(10) Patent No.: US 11,854,201 B2
(45) Date of Patent: Dec. 26, 2023

(54) BIOLOGICAL TISSUE IMAGE PROCESSING SYSTEM, AND MACHINE LEARNING METHOD

(71) Applicant: NIKON CORPORATION, Tokyo (JP)

(72) Inventors: Kohki Konishi, Yokohama (JP); Mitsuo Suga, Akishima (JP); Hideo Nishioka, Akishima (JP)

(73) Assignee: NIKON CORPORATION, Tokyo (JP)

( * ) Notice: Subject to any disclaimer, the term of this patent is extended or adjusted under 35 U.S.C. 154(b) by 409 days.

(21) Appl. No.: 17/101,267

(22) Filed: Nov. 23, 2020

(65) Prior Publication Data

US 2021/0073992 A1 Mar. 11, 2021

Related U.S. Application Data

(63) Continuation of application No. PCT/JP2019/019740, filed on May 17, 2019.

(30) Foreign Application Priority Data

May 24, 2018 (JP) .................................. 2018-099387

(51) Int. Cl.
*G06K 9/00* (2022.01)
*G06T 7/00* (2017.01)
(Continued)

(52) U.S. Cl.
CPC ....... *G06T 7/0014* (2013.01); *G01N 33/4833* (2013.01); *G06V 10/454* (2022.01);
(Continued)

(58) Field of Classification Search
CPC ........... G06T 2207/20081; G06T 2207/10056; G06T 2207/10061; G06T 2207/30024;
(Continued)

(56) References Cited

U.S. PATENT DOCUMENTS

2017/0161891 A1* 6/2017 Madabhushi ....... G06F 18/2411
2017/0167965 A1 6/2017 Wakui (Continued)

FOREIGN PATENT DOCUMENTS

JP 2016-067287 A 5/2016

OTHER PUBLICATIONS

Daisuke Koga et al., "Serial Section Scanning Electron Microscopy and Its Application for the Morphological Analysis of the Golgi Apparatus", Kenbikyo, vol. 49, No. 3 (2014).

(Continued)

*Primary Examiner* — Atiba O Fitzpatrick
(74) *Attorney, Agent, or Firm* — Foley & Lardner LLP

(57) ABSTRACT

A current observation area is determined exploratorily from among a plurality of candidate areas, on the basis of a plurality of observed areas in a biological tissue. A plurality of reference images obtained by means of low-magnification observation of the biological tissue are utilized at this time. A learning image is acquired by means of high-magnification observation of the determined current observation area. A plurality of convolution filters included in an estimator can be utilized to evaluate the plurality of candidate areas.

7 Claims, 11 Drawing Sheets

(51) Int. Cl.

| | |
|---|---|
| G01N 33/483 | (2006.01) |
| H01J 37/20 | (2006.01) |
| H01J 37/22 | (2006.01) |
| H01J 37/28 | (2006.01) |
| G06V 20/69 | (2022.01) |
| G06V 10/764 | (2022.01) |
| G06V 10/82 | (2022.01) |
| G06V 10/44 | (2022.01) |
| G01N 23/2251 | (2018.01) |

(52) U.S. Cl.
CPC ............ *G06V 10/764* (2022.01); *G06V 10/82* (2022.01); *G06V 20/693* (2022.01); *G06V 20/695* (2022.01); *G06V 20/698* (2022.01); *H01J 37/20* (2013.01); *H01J 37/222* (2013.01); *H01J 37/28* (2013.01); *G01N 23/2251* (2013.01); *G06T 2207/10056* (2013.01); *G06T 2207/20081* (2013.01); *G06T 2207/30024* (2013.01); *G06V 2201/03* (2022.01); *H01J 2237/202* (2013.01); *H01J 2237/221* (2013.01)

(58) Field of Classification Search
CPC ........... G06T 7/0014; G06T 7/11; G06T 7/74; G06T 2207/20021; G06T 7/337; G06F 18/214; G06F 18/2155; G06F 18/217; G06F 18/2178; G06F 18/2185; G06N 3/08; G06N 3/088; G06N 3/091; G01N 23/2251; G01N 21/6458; G02B 21/365; G02B 21/367; G02B 21/008; G02B 21/244; G06V 20/69; G06V 2201/122

See application file for complete search history.

(56) References Cited

U.S. PATENT DOCUMENTS

| | | | | |
|---|---|---|---|---|
| 2019/0355113 | A1* | 11/2019 | Wirch | G06T 7/0012 |
| 2020/0035350 | A1* | 1/2020 | Sullivan | G06T 7/0014 |
| 2020/0326526 | A1* | 10/2020 | Yeh | G02B 21/365 |
| 2021/0043331 | A1* | 2/2021 | Ozcan | G06V 10/82 |
| 2022/0114711 | A1* | 4/2022 | Ozcan | G06T 3/4076 |

OTHER PUBLICATIONS

Kenshi Uchihashi et al., "Neuronal cell membrane segmentation from electron microscopy images using a hostile generation model", Proceedings of the 31st Annual Conference of the Japanese Society for Artificial Intelligence, 4K1-4in2, 2017, pp. 1-4.

Benjamin Titze et al., "Volume scanning electron microscopy for imaging biological ultrastructure", Biology of the Cell, Elsevier, Paris, FR, vol. 108, No. 11, Aug. 12, 2016 (Aug. 12, 2016), pp. 307-323, XP071518937.

Burr Settles, "Active Learning Literature Survey", Jan. 26, 2010 (Jan. 26, 2010), XP055219798, http://burrsettles.com/pub/settles.activelearning.pdf (section 3.1) (67 pgs).

Extended European Search Report in Application No. 19806542.7 dated Jun. 1, 2022 (14 pgs).

Gong Zhiqiang et al., "Diversity in Machine Learning", arxiv.org, May 15, 2019 (May 15, 2019), pp. 1-28, XP055923700, https://arxiv.org/pdf/1807.01477.pdf (sections I, II, III).

Mi Lu et al., "Learning Guided Electron Microscopy with Active Acquisition : 23rd International Conference, Lima, Peru, Oct. 4-8, 2020, Proceedings, Part V," in "Pattern Recognition : 5th Asian Conference, ACPR 2019, Auckland, New Zealand, Nov. 26-29, 2019, Revised Selected Papers, Part II", Sep. 29, 2020 (Sep. 29, 2020), Springer International Publishing, Cham, XP055923702, ISSN: 0302-9743 ISBN: 978-3-030-41298-2, vol. 12265, pp. 77-87, DOI: 10.1007/978-3-030-59722-1_8, https://link.springer.com/content/pdf/10.1007/978-3-030-59722-1_8.pdf.

Notice of Refusal for Japanese Patent Application No. 2018-099387 dated May 10, 2022 and English translation thereof (6 pgs).

Paul Sujoy et al., "Efficient selection of informative and diverse training samples with applications in scene classification", 2016 IEEE International Conference On Image Processing (ICIP), IEEE, Sep. 25, 2016 (Sep. 25, 2016), pp. 494-498, XP033016532.

Raku Son et al., "Morphemics via Next-generation Electron Microscopy", arxiv.org, Cornell University Library, 201 Olin Library Cornell University Ithaca, NY 14853, Nov. 29, 2021 (Nov. 29, 2021), XP091106318 (sections 7.3, 7.4) (57 pgs).

Ronneberger Olaf et al., "U-Net: Convolutional Networks for Biomedical Image Segmentation" May 18, 2015 (May 18, 2015), pp. 1-8, XP055835587, https://arxiv.org/pdf/1505.04597.pdf.

Tao Zeng et al., "DeepEM3D: approaching human-level performance on 3D anisotropic EM image segmentation", Bioinformatics, vol. 33, No. 16, Mar. 30, 2017 (Mar. 30, 2017), pp. 2555-2562, XP055697975.

Zhang Cheng et al., "Determinantal Point Processes for Mini-Batch Diversification", Aug. 23, 2017 (Aug. 23, 2017), pp. 1-13, XP055922798, https://arxiv.org/pdf/1705.00607.pdf.

* cited by examiner

BIOLOGICAL TISSUE IMAGE PROCESSING SYSTEM, AND MACHINE LEARNING METHOD

CROSS-REFERENCE TO RELATED APPLICATION

The present application is a continuation under 35 U.S.C. § 120 of PCT/JP2019/019740, filed May 17, 2019, which is incorporated herein by reference and which claimed priority to Japanese Patent Application No. 2018-099387 filed May 24, 2018. The present application likewise claims priority under 35 U.S.C. § 119 to Japanese Patent Application No. 2018-099387 filed May 24, 2018, the entire content of which is also incorporated herein by reference.

TECHNICAL FIELD

The present disclosure relates to a biological tissue image processing system and to a machine learning method.

BACKGROUND

Three-dimensional microscopy is known as a method for analyzing or imaging three-dimensional structures of biological tissue. Three-dimensional microscopy is typically performed using an electron microscope or an optical microscope. As examples of three-dimensional microscopy for which a scanning electron microscope is used, focused ion beam SEM (FIB-SEM), serial block face SEM (SBF-SEM), and serial section SEM (see Non-Patent Document 1) have been proposed. Serial section SEM is also called array tomography.

In serial section SEM, a biological tissue sample is cut into slices, that is, a plurality of sample sections (ultrathin sections) that are successive in the depth direction, and those sections are arranged on a substrate. The sample sections arranged on the substrate are sequentially observed using a scanning electron microscope to thereby obtain a plurality of images. Based on the plurality of images obtained, a three-dimensional structure of a particular organ (such as a cell, a mitochondrion, or a nucleus) included in biological tissue is analyzed or imaged. Serial section SEM can observe an already observed sample section again.

CITATION LIST

Non Patent Literature

Non-Patent Document 1: Koga et al., "Serial Section Scanning Electron Microscopy and Its Application for the Morphological Analysis of the Golgi Apparatus", KENBIKYO, Vol. 49, No. 3, 2014.

SUMMARY

For processing images that are obtained through observation of biological tissue, a machine learning-based estimator may be used to detect or identify a target component, such as a cell, a cell membrane, or a particular organelle in a cell. In that case, it is preferable that, in a learning process of the estimator, the learning of the estimator is executed appropriately or efficiently. For example, it is preferable that various learning-purpose images are provided to the estimator to increase the generalization performance of the estimator.

The present disclosure is directed to enhancing the quality of learning in the learning process of the machine learning-based estimator in which a target component in biological tissue is estimated.

According to an aspect of the present disclosure, there is provided a biological tissue image processing system comprising a machine learning-based estimator for applying processing to an image obtained through observation of biological tissue using a microscope, the processing estimating a target component included in the biological tissue; a determiner for determining a current observation area in the biological tissue in a machine learning process of the estimator; and a controller for controlling operation of the microscope to cause the current observation area to be observed in the machine learning process of the estimator, wherein the determiner determines the current observation area in an exploratory manner based on an already observed area set consisting of a plurality of already observed areas in the biological tissue.

According to another aspect of the present disclosure, there is provided a machine learning method implemented in a biological tissue image processing system comprising a machine learning-based estimator for applying processing to an image obtained through high magnification observation of biological tissue using a microscope, the processing estimating a target component included in the biological tissue, the machine learning method causing the estimator to learn, the machine learning method comprising obtaining a reference image group consisting of one or a plurality of reference images through low magnification observation of the biological tissue using the microscope; calculating, for each of candidate portions in the reference image group, an evaluation value between the candidate portion and a plurality of already observed portions in the reference image group to select a particular candidate portion based on a plurality of evaluation values calculated for a plurality of candidate portions in the reference image group; controlling operation of the microscope to cause a current observation area in the biological tissue corresponding to the particular candidate portion to be observed by the microscope at a high magnification; and inputting, to the estimator, an image obtained through high magnification observation of the current observation area, the image serving as a learning-purpose image.

This method is implemented in the form of hardware functions or software functions. In the latter case, a program for performing the functions is installed into an information processing apparatus via a network or a portable storage medium. The information processing apparatus conceptually includes, for example, a personal computer and a biological tissue image processing system (including an electron microscope system and an optical microscope system).

Figure 1:
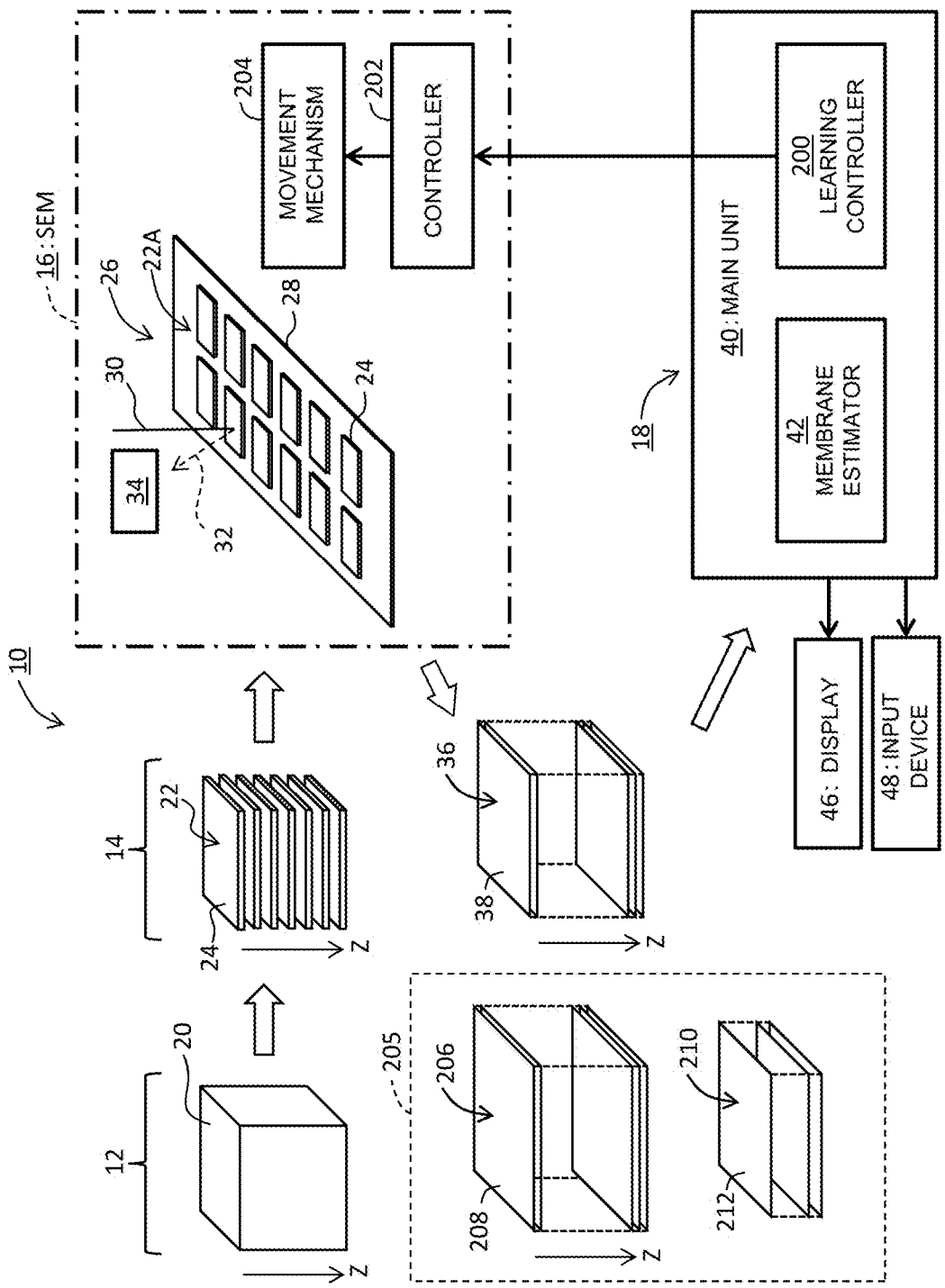
FIG. 1 is a schematic diagram illustrating a biological tissue image processing system according to an embodiment.

DESCRIPTION OF EMBODIMENTS (A) Summary of Embodiments

A biological tissue image processing system according to an embodiment includes a machine learning-based estimator, a determiner, and a controller. The estimator applies processing to an image obtained through observation of biological tissue using a microscope for estimating a target component included in the biological tissue, and obtains estimation results. The controller controls operation of the microscope to cause a current observation area in the biological tissue to be observed in a machine learning process of the estimator. The determiner determines the current observation area in the machine learning process of the estimator, and specifically determines the current observation area in an exploratory manner based on an already observed area set in the biological tissue.

With the above-described structure, the next observation target (that is, the current observation area) can be determined while taking into consideration past observation results (specifically, the already observed area set) that have been obtained in the machine learning process. As such, effective learning-purpose images can be provided to the estimator. With the above-described structure, the quality of learning of the estimator is enhanced, and, in turn, the generalization performance and the estimation accuracy of the estimator are enhanced.

The target component is a particular tissue component that is to be detected or identified during image processing. To be more precise, an image of the target component is to be detected or identified. A final analysis target or imaging target may be the target component, and another tissue component other than a final analysis target or imaging target may be the target component. In the process of, for example, imaging cytoplasm enclosed in a cell membrane, the cell membrane may first be detected or identified as the target component.

In an embodiment, the image that is input to the estimator is obtained using a scanning electron microscope. The image may be obtained using an optical microscope or another device. Although the machine learning-based estimator is composed of, for example, a CNN, another type of machine learning-based estimator may be used. Although, in an embodiment, a plurality of images are obtained by serial section SEM (array tomography), a plurality of images may be obtained by FIB-SEM, SBF-SEM, or another method. The above-described structure may be used not only for three-dimensional microscopy but also for other methods such as two-dimensional microscopy.

In an embodiment, the determiner includes an evaluation value calculation unit for calculating a plurality of evaluation values for a plurality of candidate areas based on the already observed area set; and a selector for selecting, from the plurality of candidate areas, a particular candidate area as the current observation area based on the plurality of evaluation values. With this structure, the current observation area is selected based on the evaluation values that are individually calculated for the candidate areas.

In an embodiment, the evaluation value calculation unit includes a similarity calculator for calculating, for each of the candidate areas, a plurality of similarities between the candidate area and the plurality of already observed areas; and an evaluation value calculator for calculating, for each of the candidate areas, an evaluation value based on the plurality of similarities. With this structure, a total evaluation of individual candidate areas can be obtained. The evaluation value is determined as, for example, a sum, an average value, a representative value, or another value of the plurality of similarities.

In an embodiment, the image that is input to the estimator is an image obtained through high magnification observation of the biological tissue; a reference image group consisting of one or a plurality of reference images is obtained through low magnification observation of the biological tissue; and the similarity calculator calculates the plurality of similarities based on a candidate portion in the reference image group, which corresponds to the candidate area, and a plurality of already observed portions in the reference image group, which correspond to the plurality of already observed areas. It should be understood that a high magnification is a magnification that is higher than a low magnification.

With the above-described structure, the similarities are calculated through image comparison. Methods for image comparison include, for example, a first method in which a plurality of portions in the reference image group are compared without being processed, and a second method in which a plurality of portions in the reference images are processed and then the plurality of portions that have been processed are compared. A first magnification is set for high magnification observation, and a second magnification that is lower than the first magnification is set for low magnification observation. By performing low magnification observation, an image is typically obtained quickly over a large area of a sample.

The candidate portions in the reference image group are image portions that represent the substance of the candidate areas that are ideated in the biological tissue, and the already observed portions in the reference image group are image portions that represent the substance of the already observed areas in the biological tissue. Although, in an embodiment, a reference image is composed of a low magnification image, an image other than a low magnification image may be used as a reference image. For example, a high magnification image that is obtained through high magnification observation of a large area in the biological tissue may be used as a reference image. Also, a different type of image may be used as a reference image.

In an embodiment, the similarity calculator includes a first upsampling processor for applying upsampling to the candidate portion; a second upsampling processor for applying upsampling to the plurality of already observed portions; a first filter processor for applying, to the candidate portion that has been subjected to the upsampling, at least one convolution filter that is included in the estimator; a second filter processor for applying, to the plurality of already observed portions that have been subjected to the upsampling, the at least one convolution filter that is included in the estimator; and a calculator for calculating the plurality of similarities based on the candidate portion to which the upsampling and the at least one convolution filter have been applied and the plurality of already observed portions to which the upsampling and the at least one convolution filter have been applied.

With the above-described structure, the similarities are each calculated based on two image portions that have undergone all or part of image processing (characteristic amount extraction processing) executed in the estimator. An evaluation value that has taken into consideration the characteristics of the estimator can be calculated in this manner. As a plurality of convolution filters that are included in the estimator can be taken out to the outside, the above-described structure applies all, some, or one of the plurality of convolution filters for similarity calculation as well. For example, a plurality of convolution filters that function in parallel reside in the estimator. Such a plurality of convolution filters are applied to individual candidate portions and individual already observed portions. The convolution filters in the estimator are updated as the learning process proceeds. Preferably, the latest convolution filters are used for similarity calculation. In other words, as the filter processing in the estimator changes, the filter processing in the similarity calculator changes.

In an embodiment, the similarity calculator includes an upsampling processor for applying upsampling to the candidate portion; a first filter processor for applying, to the candidate portion that has been subjected to the upsampling, at least one convolution filter that is included in the estimator; a second filter processor for applying, to a plurality of high magnification images corresponding to the plurality of already observed portions, the at least one convolution filter that is included in the estimator; and a calculator for calculating the plurality of similarities based on the candidate portion to which the upsampling and the at least one convolution filter have been applied and the plurality of high magnification images to which the at least one convolution filter has been applied. With this structure, as in the above-described structure, an evaluation value can be calculated while taking into consideration the characteristics of the estimator. Also, because the plurality of high magnification images that have been already obtained are used, applying the upsampling processing to the plurality of already observed portions can be eliminated.

In an embodiment, the plurality of reference images are obtained through low magnification observation of a plurality of biological tissue sections corresponding to a plurality of depths in the biological tissue. With this structure, the estimator can learn appropriately or efficiently in the learning process on the precondition that a plurality of images corresponding to a plurality of depths are input to the estimator in an analysis process. In an embodiment, the microscope includes a movement mechanism for moving a substrate relative to an observation optical axis, the substrate having the plurality of biological tissue sections placed thereon, and the controller controls the movement mechanism to cause the current observation area to be observed at a high magnification. The observation optical axis is, for example, an electron beam axis or an optical axis. With the substrate being fixed, the observation optical axis may be moved.

A machine learning method according to an embodiment is a machine learning method implemented in a biological tissue image processing system comprising a machine learning-based estimator for applying processing to an image obtained through high magnification observation of biological tissue using a microscope, the processing estimating a target component included in the biological tissue, the machine learning method causing the estimator to learn.

Specifically, a machine learning method according to an embodiment comprises obtaining a reference image group consisting of one or a plurality of reference images through low magnification observation of the biological tissue using the microscope; calculating, for each of candidate portions in the reference image group, an evaluation value between the candidate portion and a plurality of already observed portions in the reference image group to select a particular candidate portion based on a plurality of evaluation values calculated for a plurality of candidate portions in the reference image group; controlling operation of the microscope to cause a current observation area in the biological tissue corresponding to the particular candidate portion to be observed by the microscope at a high magnification; and inputting, to the estimator, an image obtained through high magnification observation of the current observation area, the image serving as a learning-purpose image. With this method, a high-quality learning-purpose image can be provided to the estimator. Consequently, the estimation accuracy of the estimator is enhanced.

(B) Details of Embodiments

FIG. 1 illustrates a biological tissue image processing system according to an embodiment. The illustrated biological tissue image processing system 10 is a system for analyzing or imaging a three-dimensional structure of biological tissue. This biological tissue image processing system is used to generate, for example, an image that three-dimensionally represents neurons within the brain of a human or an animal. An analysis target or an imaging target may be anything such as tissues, organs, or others in a living thing.

In an example structure illustrated in FIG. 1, the biological tissue image processing system 10 is composed of a sample pretreatment apparatus 12, a serial section preparation apparatus 14, a scanning electron microscope (SEM) 16, and a biological tissue image processing apparatus 18.

The sample pretreatment apparatus 12 is an apparatus that pretreats a piece of tissue 20 taken from a living body, or corresponds to various types of instruments for such pretreatment. Examples of the pretreatment include fixation treatment, staining treatment, conductive treatment, resin embedding treatment, and shaping treatment. All, some, or one of them are performed as necessary. In the staining treatment, for example, osmium tetroxide, uranium acetate, or lead citrate may be used. The staining treatment may be perforated on sample sections that will be described below. One, some, or all operations included in the pretreatment may be performed manually.

The serial section preparation apparatus 14 is either provided outside the SEM 16 or provided within the SEM 16. The serial section preparation apparatus 14 cuts a cubic sample that has been pretreated, into a plurality of sample sections 24 that are successive in the depth direction (Z direction). In this process, a device such as an ultramicrotome may be used. This task may be performed manually. The plurality of sample sections 24 constitute a sample section group 22. In an actual process, when a sample is cut into slices, that is, the plurality of sample sections 24, they are placed on a substrate 28 in a predetermined arrangement. The substrate 28 is, for example, a glass substrate or a silicone substrate. Although FIG. 1 illustrates a sample section array 22A consisting of two rows of sample sections placed on the substrate 28, this arrangement is illustrated merely by way of example. The substrate 28 and the sample section array 22A constitute a sample unit 26.

Each of the sample sections 24 has a height and a width on the order of, for example, nm or µm. Sample sections 24 with a larger size (on the order of, for example, mm) may also be prepared. Each of the sample sections 24 has a thickness (size in the Z direction) in a range of, for example, nanometers to hundreds of nanometers, and in an embodiment, the thickness is in a range of, for example, 30 nm to 70 nm. It should be noted that all values provided in the specification of the present application are given by way of example.

The SEM 16 includes, for example, an electron gun, a deflector (scanner), an objective lens, a sample chamber, a detector 34, a controller 202, and a movement mechanism 204. The sample chamber has therein a stage and the movement mechanism 204; the stage holds the sample unit 26, and the movement mechanism 204 moves the stage. The controller 202 controls the operation of the movement mechanism 204 and, in turn, the movement of the stage. Specifically, a particular sample section 24 selected from the sample section array 22A is illuminated with an electron beam 30. With the illumination location being scanned (for example, raster scanned), reflected electrons 32 emitted from illumination locations are detected by the detector 34. An SEM image is formed in this manner. This process is performed for each of the sample sections 24. As a result, a plurality of SEM images 38 that are results of observation of the plurality of sample sections 24 are obtained. The plurality of SEM images 38 constitute an SEM image stack 36. The SEM image stack 36 serves as an analysis target.

The SEM image stack 36 is composed of the plurality of SEM images 38 which correspond to a plurality of depths in the Z direction (in other words, the plurality of SEM images 38 which are successive in the Z direction in a data storage space). Each of the SEM images 38 serves as an original image or an input image when seen from the biological tissue image processing apparatus 18 side. Each of the SEM images 38 is electronic data, and each of the SEM images 38 is transmitted from the SEM 16 to the biological tissue image processing apparatus 18 via a network or a portable storage medium.

It should be noted that, when a direction perpendicular to the Z direction is defined as the X direction and a direction perpendicular to the Z direction and the X direction is defined as the Y direction, it is preferable that, in a biological tissue analysis process, an observation range (electron beam two-dimensional scanning range) in each of the sample sections 24 is determined such that the sample sections 24 are observed over the same X direction observation range and the same Y direction observation range. Rather than the reflected electrons 32, for example, secondary electrons may be detected. The controller 202 also has a function of varying the acceleration voltage for forming the electron beam 30 and a function of changing the magnification. The electron beam forming acceleration voltage may be switched in accordance with, for example, the biological tissue, the observation target in the biological tissue, or the purpose of observation. Typically, the same acceleration voltage is set for a learning process of a membrane estimator 42, which will be described later, and a subsequent biological tissue analysis process.

In a machine learning process of the membrane estimator 42, a plurality of sample sections for machine learning, which correspond to a plurality of depths, are prepared by a method similar to the method described above. Although it may be the case that only a single sample section is prepared for machine learning, in order to enhance the quality of learning of an estimator for three-dimensional microscopy, it is preferable that a plurality of sample sections that are successive in the depth direction as described above are prepared.

In a primary learning (initial learning) process, a plurality of observation areas that are set at random in a plurality of sample sections are observed at a high magnification, so that a plurality of initial learning-purpose images (not illustrated) serving as a plurality of high magnification images are obtained. These images are used to execute the primary learning of the membrane estimator 42. In this process, the plurality of initial learning-purpose images are transmitted from the SEM 16 to the biological tissue image processing apparatus 18 via a network or a portable storage medium. These initial learning-purpose images may be transmitted to a different apparatus for preparing a correct image. Details of the primary learning process will be described later.

Subsequently, a reference image group (reference image stack) 206 is obtained either before execution of a secondary learning process or in an initial step of the secondary learning process. Specifically, each of the learning-purpose sample sections is observed at a low magnification either overall or over its relatively large area portion. A plurality of reference images (low magnification images) 208 corresponding to a plurality of sample sections are obtained in this manner. These reference images 208 constitute the reference image group 206. The high magnification is a first magnification, and the low magnification is a second magnification that is lower than the first magnification. The plurality of reference images 208 are obtained in order to determine, in an exploratory manner, one or a plurality of current observation areas that are to be observed at a high magnification in the secondary learning process of the membrane estimator 42.

In the secondary learning process, in order to enhance the quality of learning of the membrane estimator 42, or in order to provide various learning-purpose images to the membrane estimator 42, a plurality of current observation areas are determined from a plurality of sample sections in an exploratory manner based on the reference image group 206 by a method that will be described later. The plurality of current observation areas are then observed at a high magnification. A plurality of learning-purpose images 212 serving as a plurality of high magnification images are obtained in this manner. These images constitute a learning-purpose image group 210. The learning-purpose image group 210 is used to execute the secondary learning of the membrane estimator 42. Obtaining the learning-purpose image group 210 and using it for the secondary learning of the membrane estimator 42 are repeatedly executed up until a certain membrane estimation accuracy is obtained. The reference image group 206 and the learning-purpose image group 210 constitute an image set 205 for the secondary learning process. The reference image group 206 and the learning-purpose image group 210 are also transmitted from the SEM 16 to the biological tissue image processing apparatus 18 via a network or a portable storage medium. Details of the secondary learning process will also be described later.

The biological tissue image processing apparatus 18 is, in the illustrated example structure, composed of a personal computer. The biological tissue image processing apparatus 18 may be incorporated into the SEM 16, and the biological tissue image processing apparatus 18 may be incorporated into a system computer that controls, for example, the SEM 16. The SEM 16 may be controlled by the biological tissue image processing apparatus 18.

The biological tissue image processing apparatus 18 includes a main unit 40, a display 46, and an input device 48.

A plurality of functions of the main unit 40 will be described in detail later with reference to FIG. 2 and subsequent figures. In FIG. 1, each of two representative functions (membrane estimation function and learning control function) that are exercised by the main unit 40 is expressed in the form of a block. Specifically, the main unit 40 includes the machine learning-based membrane estimator 42 and a learning controller 200. The display 46 is composed of, for example, an LCD or an organic EL display device. The input device 48 is composed of, for example, a keyboard or a pointing device that is operated by a user.

As described above, according to the present embodiment, in the secondary learning process, the learning controller 200 determines a plurality of current observation areas in an exploratory manner. The controller 202 in the SEM 16 either controls the movement mechanism 204 or controls the observation magnification so as to sequentially observe the plurality of current observation areas in the plurality of sample sections 24 at a high magnification. As a result of high magnification observation of the plurality of current observation areas, the plurality of learning-purpose images 212 serving as a plurality of high magnification images are obtained. These images are used to execute the secondary learning of the membrane estimator 42.

Figure 2:
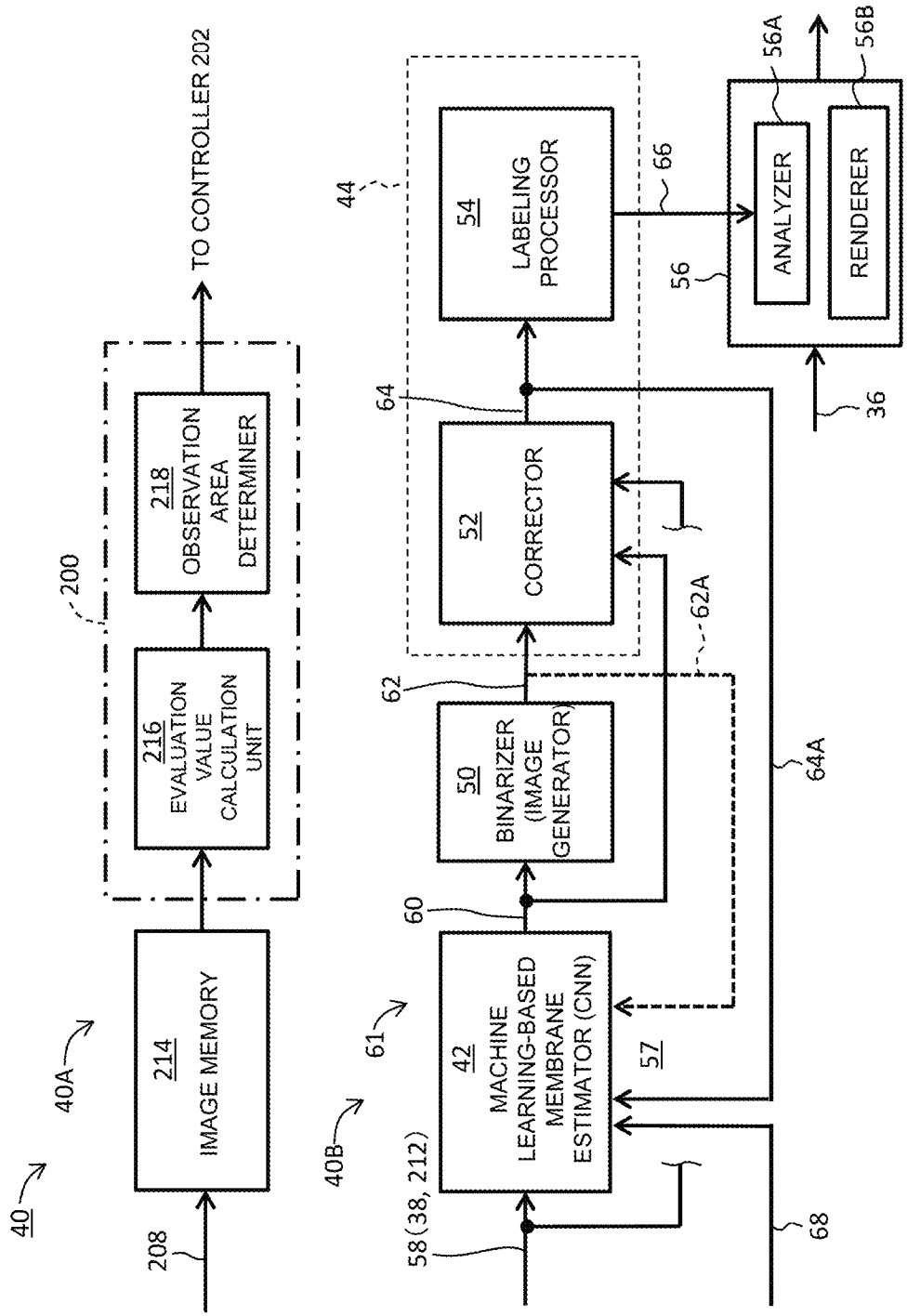
FIG. 2 is a block diagram illustrating a first example structure of a main unit of a biological tissue image processing apparatus.

FIG. 2 illustrates a first example structure of the main unit 40. The main unit 40 generally consists of a learning control subsystem 40A and an image processing subsystem 40B. The latter of them, the image processing subsystem 40B, will first be described below.

The image processing subsystem 40B includes, for example, the machine learning-based membrane estimator 42, a binarizer (image generator) 50, a process tool unit (task assistant) 44, and a volume data processor 56. The process tool unit 44 includes a corrector 52 and a labeling processor 54. The volume data processor 56 includes an analyzer 56A and a renderer 56B.

The substance of the structures illustrated in FIG. 2, except those corresponding to user's tasks or actions, is basically software or, in other words, a program that is executed by a general-purpose processor such as a CPU or a GPU. Still, one, some, or all of these structures may be implemented by a special-purpose processor or other hardware. All, some, or one of the functions of the biological tissue image processing apparatus may be executed by one or a plurality of information processing devices that reside on a network.

The membrane estimator 42 serves as membrane estimation means. The membrane estimator 42 applies membrane estimation processing to an input original image (SEM image or high magnification image) 58, and thereby outputs a membrane likelihood map 60. In the illustrated example structure, the membrane estimator 42 is composed of a convolutional neural network (CNN). Its specific example structure will be described later with reference to FIG. 3. To correctly estimate a membrane using the CNN, an actual operation of the CNN is preceded by a CNN learning process, which is executed beforehand. The learning process includes, as described above, the primary learning process (initial learning process) and the secondary learning process.

In the primary learning process, a plurality of image pairs that constitute teacher data are provided to the membrane estimator 42 to thereby improve (optimize) a CNN parameter group in the membrane estimator 42. In other words, the membrane estimator 42 accumulates machine learning results. Here, each image pair is composed of the original image (SEM image or high magnification image) 58 and its corresponding correct image 68. The correct image 68 is prepared by, for example, a manual operation performed on the original image 58. The correct image 68 may be prepared from the original image 58 using, for example, an unsupervised machine learner or a simple identifier such as a support vector machine (SVM). In this case, the original image 58 is input to such an identifier, and when, based on its output, a user can determine that the identifier works to some degree, the output may be used as the correct image 68. The correct image 68 may be prepared based on an output from the membrane estimator 42 that has undergone a certain primary learning process.

In the subsequent secondary learning process, a plurality of image pairs serving as teacher data are provided to the membrane estimator 42 in a similar manner as in the primary learning process on the precondition that the membrane estimator 42 works to some degree as it has undergone the primary learning process. In an embodiment, the teacher data are composed of the plurality of image pairs that are used in the primary learning process and the plurality of image pairs that are added in the secondary learning process. Each image pair that is added consists of an original image 58 (specifically, learning-purpose image 212 described above) and its corresponding correct image 64A. The correct image 64A is prepared by the biological tissue image processing apparatus itself, that is, the structures from the membrane estimator 42 to the process tool unit 44. Specifically, in response to an input of the original image 58 to the membrane estimator 42, the membrane estimator 42 outputs the membrane likelihood map 60 as an estimation result image. The correct image 64A is prepared through generation of a temporary membrane image based on the membrane likelihood map 60 and correction of the temporary membrane image 62 by a user (expert) using the process tool unit 44. Individual processing will be described in detail later. The temporary membrane image 62 may be used as a correct image 62A. The secondary learning process further improves the CNN parameter group in the membrane estimator 42. In other words, the membrane estimator 42 further accumulates machine learning results. The secondary learning process ends when it is determined that, for example, a result of estimation processing performed on the original image 58 is sufficiently similar to the correct images 68 and 64A corresponding to the original image 58. After that, re-learning of the membrane estimator 42 is executed as necessary by a method similar to the method described above.

In the secondary learning process, because correct images can be prepared on the basis of membrane estimation results, the user's workload is significantly reduced as compared to the case where a correct image is prepared overall manually from an original image. This also holds true in a learning process that is necessary after the secondary learning process. It should be noted that, in the primary learning process and the secondary learning process, a plurality of image pairs may be collectively provided to the membrane estimator 42 to be subjected to batch processing.

A database 57 stores a plurality of original images 58 and a plurality of correct images 68 and 64A. The membrane estimator 42 and the database 57 may be integral with each other. The machine learning-based membrane estimator may be implemented using U-net, or may be implemented using, for example, an SVM or random forest.

The binarizer 50 serves as an image generator. Specifically, the binarizer 50 is a module that generates the temporary membrane image 62 by performing binarization processing on the membrane likelihood map 60, as will be described later by way of example with reference to FIG. 4.

The membrane likelihood map 60 consists of a two-dimensional arrangement of a plurality of membrane likelihoods. Each of the membrane likelihoods is a value that represents a probability of being a membrane. The membrane likelihoods range, for example, from 0 to 1. The membrane likelihood map 60 can be interpreted as a membrane likelihood image. In an embodiment, a threshold value is set in the binarizer 50, and the binarizer 50 converts to 1 a membrane likelihood that is greater than or equal to the threshold value, and converts to 0 a membrane likelihood that is less than the threshold value. An image thereby generated is the temporary membrane image 62. In an embodiment, to differentiate membrane images that have yet to be corrected from membrane images that have been corrected, membrane images that have yet to be corrected are referred to as temporary membrane images 62 for simplicity and ease of description.

It should be noted that the membrane estimator 42 and the binarizer 50 constitute an image generator 61. The image generator 61 may overall be composed of, for example, a CNN. In that case as well, step-by-step generation of the membrane likelihood map and the temporary membrane image can be ideated. The temporary membrane image 62 can also be used as the correct image 62A. Before the binarization processing, noise removal, edge enhancement, or other processing may be applied to the membrane likelihood map 60.

The process tool unit 44 serves as a task assistant or task assistance means. In terms of information processing, the process tool unit 44 has a display processing function and an image processing function. In terms of tasks, the process tool unit 44 has a correction function and a labeling function, and in FIG. 2, these functions are represented as the corrector 52 and the labeling processor 54.

Via a task window illustrated by way of example in FIG. 5, which will be described later, the corrector 52 displays to a user a temporary membrane image that is being a task target, as a task target image, and receives user's correction instructions on the task target image. The temporary membrane image that is being the task target image is modified as corrected. When the task target image contains, for example, a membrane break, a membrane pixel group is added to the break. When the task target image contains, for example, a portion that is not a membrane and that is misrecognized as a membrane, a membrane pixel group that constitutes that portion is deleted. In the process of such addition and deletion, the corrector 52 serves as a module that assists the user in performing a task or an operation and manages temporary membrane images.

In the illustrated example structure, the temporary membrane image 62, which is generated, the original image 58, which is input, and the membrane likelihood map 60, which is generated, are input in parallel to the corrector 52 (or the process tool unit 44). As such, the original image 58 or the membrane likelihood map 60 corresponding to the task target image can be displayed either together with or instead of the temporary membrane image serving as the task target image.

The labeling processor 54 is a module for performing labeling (painting and labeling) on individual regions (cell lumina) included in a membrane image that has been corrected (or a membrane image for which correction has not been completed). Labeling includes manual labeling performed by a user and automatic labeling. Upon the completion of the correction task and the labeling task, three-dimensional labeling data 66 that differentiate between cell lumina and other regions are created. The three-dimensional labeling data 66 are transmitted to the volume data processor 56. Labeling will be described later with reference to FIG. 6.

In the illustrated example structure, an original image stack (SEM image stack) 36 consisting of a plurality of original images is input to the volume data processor 56. The original image stack 36 constitutes volume data. As described above, the three-dimensional labeling data 66 are also input to the volume data processor 56. These data also are a type of volume data.

The analyzer 56A analyzes a target organ (for example, neuron) based on, for example, the three-dimensional labeling data 66. For example, the shape, volume, length, and other characteristics may be analyzed. In this process, the original image stack 36 is analyzed with reference to the three-dimensional labeling data. The renderer 56B forms a three-dimensional image (stereoscopically rendered image) based on the three-dimensional labeling data 66. For example, a portion that is to be imaged may be extracted from the original image stack 36 based on the three-dimensional labeling data 66, and rendering processing may be applied to the extracted portion.

In the above-described secondary learning process, membrane images 64 that have been corrected are individually input to the membrane estimator 42 as correct images 64A. In the process of preparation of the correct images 64A, because results of estimation performed by the membrane estimator 42 may be used, and because the process tool unit 44 may be used, the workload for preparation of each of the correct images 64A is significantly reduced compared to the case where they are not used. In other words, the above-described structure can reduce effort and time that are required in a learning process of the membrane estimator 42. In an analysis process that follows the secondary learning process, as a result of combined use of the membrane estimator 42 and the process tool unit 44, the quality of an image group that is an analysis target or a rendering target can be enhanced, and the image group can be generated easily and quickly.

The learning control subsystem 40A in FIG. 2 will next be described below. In an embodiment, the learning control subsystem 40A functions in the secondary learning process. The learning control subsystem 40A may function in a subsequent learning process. The learning control subsystem 40A may function in the primary learning process. An image memory 214 stores a plurality of reference images 208. The image memory 214 may be integral with the above-described database 57.

The learning controller 200 serves as learning control means and includes an evaluation value calculation unit 216 and an observation area determiner 218. The evaluation value calculation unit 216 serves as evaluation value calculation means or serves as a similarity calculator and an evaluation value calculator, and calculates a plurality of evaluation values for a plurality of candidate areas. In an embodiment, each of the evaluation values is a similarity evaluation value. A plurality of similarities are calculated for the individual candidate areas between the candidate areas and a plurality of already observed areas. Evaluation values are calculated for the individual candidate areas based on the plurality of similarities. An evaluation value is an index that represents the degree to which a candidate area is similar to an already observed area set.

The observation area determiner 218 serves as observation area determination means or selection means, and determines or selects one or a plurality of candidate areas as one or a plurality of current observation areas based on a plurality of evaluation values that are calculated for a plurality of candidate areas. In an embodiment, to reduce the amount of calculation, a plurality of current observation areas are determined in a single instance of processing. More specifically, to provide diversity in a learning-purpose image set in the secondary learning process, a plurality of candidate areas having low similarities are selected in an exploratory manner. Coordinate information for each of the current observation areas is transmitted to the controller 202 in the SEM.

Specific processing in the learning controller 200 will be described in detail later with reference to FIG. 7 and subsequent figures. The learning controller 200 may be provided in the SEM or in a system control apparatus.

Figure 3:
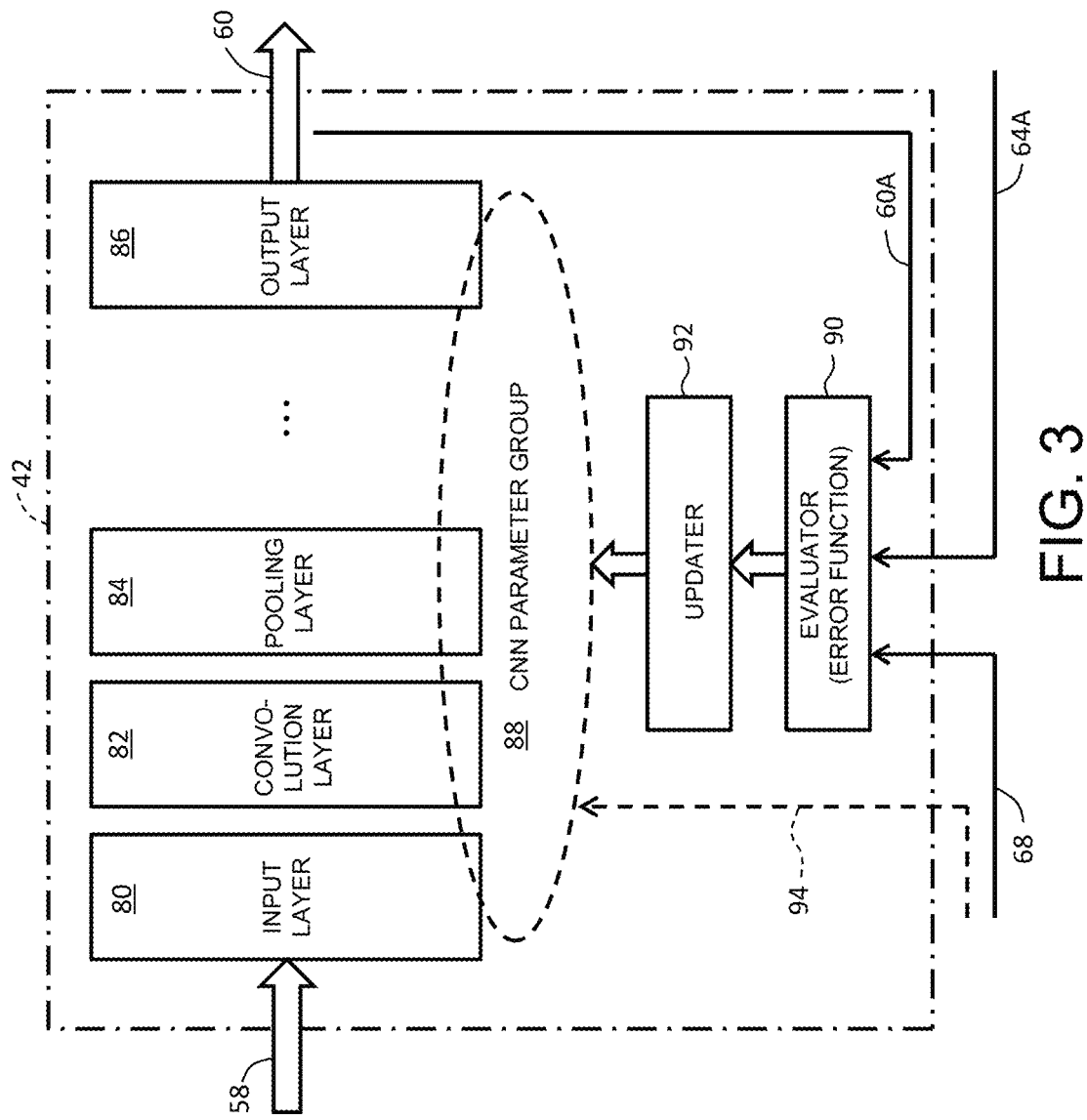
FIG. 3 is a block diagram illustrating an example structure of a machine learning-based membrane estimator.

FIG. 3 schematically illustrates an example structure of the membrane estimator 42. The membrane estimator 42 includes a plurality of layers, such as an input layer 80, a convolution layer 82, a pooling layer 84, and an output layer 86. These layers function according to a CNN parameter group 88. The CNN parameter group 88 includes a plurality of weighting factors, a plurality of bias values, and other parameters. The CNN parameter group 88 is initially composed of an initial value group 94. The initial value group 94 is generated using, for example, random numbers. The membrane estimator 42 typically includes convolution layers. Each convolution layer includes one or a plurality of convolution filters.

An evaluator 90 and an updater 92 function in a learning process. For example, the evaluator 90 calculates an evaluation value based on a plurality of image pairs (original images 58 and their corresponding correct images 68 and 64A) that constitute teacher data. Specifically, an evaluation value is calculated by sequentially inputting to an error function results 60A of estimation processing performed on the original images 58 and the correct images 68 and 64A corresponding to the original images 58. The updater 92 updates the CNN parameter group 88 so as to improve the evaluation value. By repeating this process, the CNN parameter group 88 is optimized overall. In an actual process, at the time when the evaluation value has reached a certain value, it is determined that the learning process should end. The structure illustrated in FIG. 3 is given merely by way of example, and estimators having various structures can be used as the membrane estimator 42.

Figure 4:
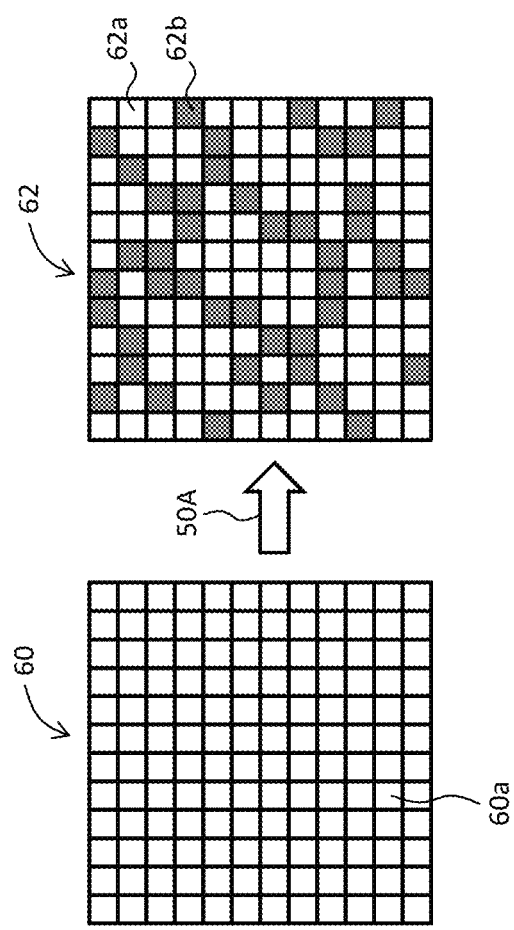
FIG. 4 illustrates generation of a temporary membrane image based on a membrane likelihood map.

FIG. 4 illustrates the function of a binarizer. The membrane estimator outputs the membrane likelihood map 60. The membrane likelihood map 60 consists of a plurality of membrane likelihoods 60a corresponding to a plurality of pixels, and each of the membrane likelihoods 60a is a value that represents a probability of being a membrane. As illustrated by reference numeral 50A, the binarizer binarizes the membrane likelihood map 60 to thereby generate a temporary membrane image 62 in the form of a binarized image. In the process of binarization, the individual membrane likelihoods 60a are compared with a threshold value. For example, membrane likelihoods 60a that are greater than or equal to the threshold value are converted to pixels 62a each having a value of 1, and membrane likelihoods 60a that are less than the threshold value are converted to pixels 62b each having a value of 0. The pixels 62a are treated as pixels that constitute a membrane (membrane pixels). The threshold value may be variably set by a user. This setting may be automated. For example, the threshold value may be varied while the temporary membrane image 62 is being observed.

Figure 5:
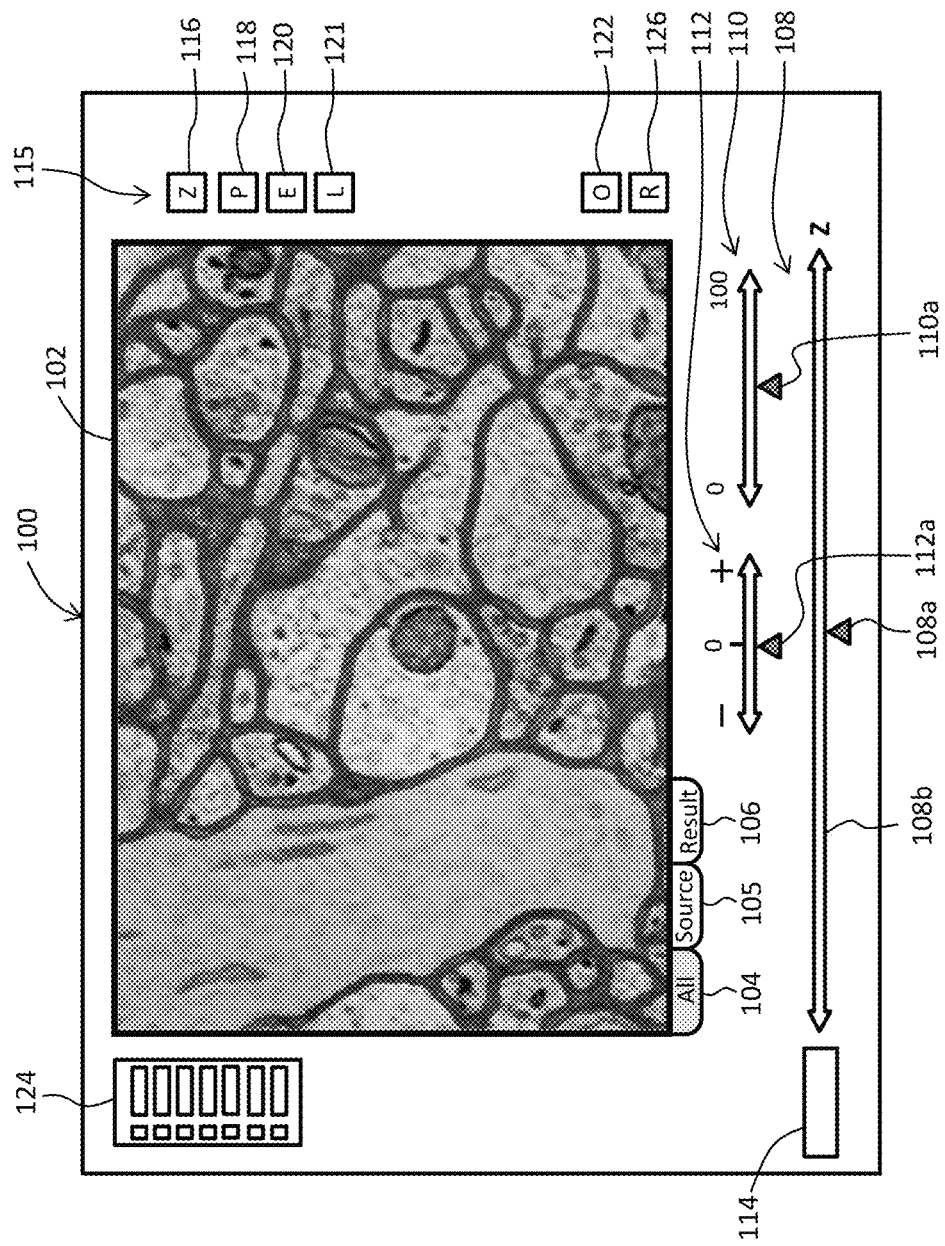
FIG. 5 illustrates a task window.

FIG. 5 illustrates an example of a task window that is displayed by a process tool unit. In the illustrated example, a task window 100 includes a display image 102. The display image 102 is a combined image (composite image) that consists of a temporary membrane image (task target image) and an original image corresponding to a depth that is selected by a user. An original image which is a gray scale image constitutes a background image, and a temporary membrane image (task target image) which is a color image (for example, a blue image) is displayed superimposed on the background image. In the illustrated display image 102, which represents brain tissue, a plurality of cell's cross sections appear. Also, cross sections of organelles (for example, mitochondria) in cells also appear.

When a tab 104 is selected, the display image 102 described above is displayed. When a tab 105 is selected, only the original image which is a gray scale image is displayed. When a tab 106 is selected, only a membrane likelihood map (membrane likelihood image) which is a gray scale image is displayed. Observation of the membrane likelihood map enables confirmation as to, for example, whether the threshold value is set appropriately. The original image that is displayed alone facilitates specifically observing details of the membrane. A tab that causes displaying only a temporary membrane image serving as a task target image may be added. A membrane likelihood map may be used as a background image, and a temporary membrane image may be displayed superimposed on the background image.

A depth selection tool 108 is a display component (operation component) for selecting a particular depth (display depth) in the Z direction. The depth selection tool 108 consists of a Z-axis symbol 108b that represents the Z axis, and a marker 108a that serves as a slider that is slidably movable along the Z-axis symbol 108b. By moving the marker 108a, a desired depth can be selected. Such a depth selection tool 108 provides advantages in that the depth to be selected or the amount of change in depth can be recognized easily and intuitively. It should be noted that the left end point of the Z-axis symbol 108b corresponds to a depth of zero, and the right end point of the Z-axis symbol 108b corresponds to a maximum depth. A depth selection tool having a different form may be used. A depth input field 114 is a field that is used to directly specify a depth in a numerical form. A currently selected depth may be displayed in the depth input field 114 in a numerical form.

A transparency adjustment tool 110 is a tool that is used to adjust the transparency (display weight) of a color temporary membrane image (task target image) that is being displayed combined with the display image 102 that is also being displayed. For example, when a marker 110a is moved to the left, the color temporary membrane image comes to have a lower display weight and an increased transparency, so that the original image is displayed predominantly. Conversely, when the marker 110a is moved to the right, the color temporary membrane image comes to have a greater display weight and a reduced transparency, so that the color temporary membrane image is rendered more clearly.

A superposition display tool 112 is operated when a currently displayed image (combined image, original image, or membrane likelihood map) is displayed to have superposed thereon either an image (combined image, original image, or membrane likelihood map) that is adjacent on the shallower side in the depth direction or an image (combined image, original image, or membrane likelihood map) that is adjacent on the deeper side in the depth direction. When a marker 112a is moved to the left, the image that is adjacent on the shallower side comes to have a greater display weight, and conversely, when the marker 112a is moved to the right, the image that is adjacent on the deeper side comes to have a greater display weight. Three or more images may be displayed superposed on one another. It should be understood that, if too many images are superposed on one another, the resulting image would be too complicated; therefore, it is preferable that a small number of images are superposed on one another. By displaying images superposed on one another as described above, spatial information is obtained easily.

A button column 115 is composed of a plurality of virtual buttons 116, 118, 120, 121, 122, and 126. The button 116 is a display component that is operated when an image is zoomed (zoomed in or out). The button 118 is a display component that is operated when a pen tool is used. When the button 118 is turned on, the shape of the cursor changes to a pen shape, and with this pen, membrane pixels can be added. The size of the pen can be changed. The button 120 is a display component that is operated when an eraser is used. When the button 120 is turned on, the shape of the cursor changes to an eraser shape, and with this eraser, membrane pixels can be deleted. The size of the eraser can be changed.

The button 121 is a display component that is operated when painting is performed. With the button 121 turned on, designating a region causes that region to be painted over. Also, upon operation of the button 121, a desired function can be selected from a plurality of functions that are provided for painting (or labeling). Upon operation of the object numbering (labeling) button 122, a color palette 124 is displayed. For example, a color that is selected from the color palette is assigned to a region for which painting processing has been performed. As a result, that region is colored with the selected color. Individual colors are each associated with an object number. By assigning the same color, that is, the same object number, to a plurality of regions across layers, three-dimensional lumen regions in particular cells are defined by those regions.

The button 126 is a black and white inversion button. Upon operation of this button, in a displayed image, portions that are displayed in black turn white, and conversely, portions that are displayed in white turn black.

An additional button may be preferably provided for displaying a three-dimensional image. The content of the task window 100 illustrated in FIG. 5 is given merely by way of example; the content may be preferably determined as appropriate such that, when a user performs a task, the ease of performance is good. For example, a three-dimensional image that represents labeling results may be displayed.

Figure 6:
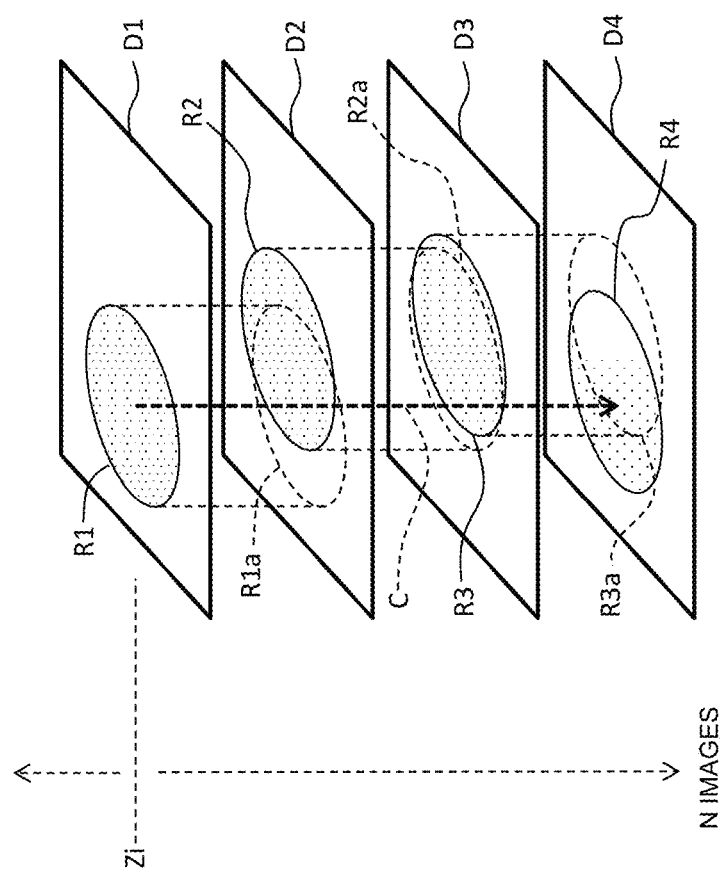
FIG. 6 illustrates an example of labeling processing.

FIG. 6 illustrates an example of three-dimensional joining processing included in the labeling processing. FIG. 6 illustrates a plurality of temporary membrane images D1 to D4 that are successive in the Z direction. The temporary membrane image D1 corresponding to a depth Zi is a task target image. This image is a criterion image in processing that will be described below.

In a first example of three-dimensional joining processing, a representative point is identified for a region R1 included in the temporary membrane image D1 which is a criterion image. For example, a center point or a center of gravity point is identified as a representative point. Subsequently, a perpendicular line C that passes through the representative point is defined. Referring to a number N of temporary membrane images found, for example, on the deeper side from the criterion image, regions through which the perpendicular line C passes are identified in those images. Regions R1, R2, R3, R4, . . . through which perpendicular line C passes are assigned the same label.

Also, the above-described processing may be applied to a number N of temporary membrane images found on the shallower side from the criterion image. Results of automatic labeling are typically checked visually by a user.

In a second example of three-dimensional joining processing, the region R1 (its outer edge) included in the temporary membrane image D1 which is a criterion image is projected on the temporary membrane image D2, and a projection region R1$a$ is defined. On the temporary membrane image D2, the region R2 that includes a largest overlap with the projection region R1$a$ is identified. Subsequently, the region R2 is projected on the temporary membrane image D3, and a projection region R2$a$ is defined. On the temporary membrane image D3, the region R3 that includes a largest overlap with the projection region R2$a$ is identified. Similarly, on the temporary membrane image D4, a projection region R3$a$ is defined, and the region R4 is identified based on the projection region R3$a$. The region R1 and the regions R2, R3, and R4 that are identified using the region R1 as the starting point are all assigned the same label.

Although, in the above-described processing, the projection source region is updated each time the layer is changed, the projection source region may be fixed. For example, the region R1 may be projected on the temporary membrane images D2, D3, and D4. Also, although, in the above-described processing, joint targets are searched for on one side in the Z direction from the criterion image, joint targets may be searched for on both sides in the Z direction from the criterion image. The search range may be selected by a user. In any case, results of automatic labeling are typically checked visually by a user. In that process, the task window illustrated in FIG. 5 is used.

The above-described three-dimensional joining processing is described merely by way of example, and three-dimensional joining processing other than that described above may be used. To identify the relationship of joints between regions, one or a plurality of characteristic amounts for each region may be used. As examples of region characteristic amounts, the area, the shape, the perimeter, the location of the center of gravity, the luminance histogram, and the texture may be used. Alternatively, as examples of characteristic amounts between regions, the overlap area and the distance between representative points may be used.

Figure 7:
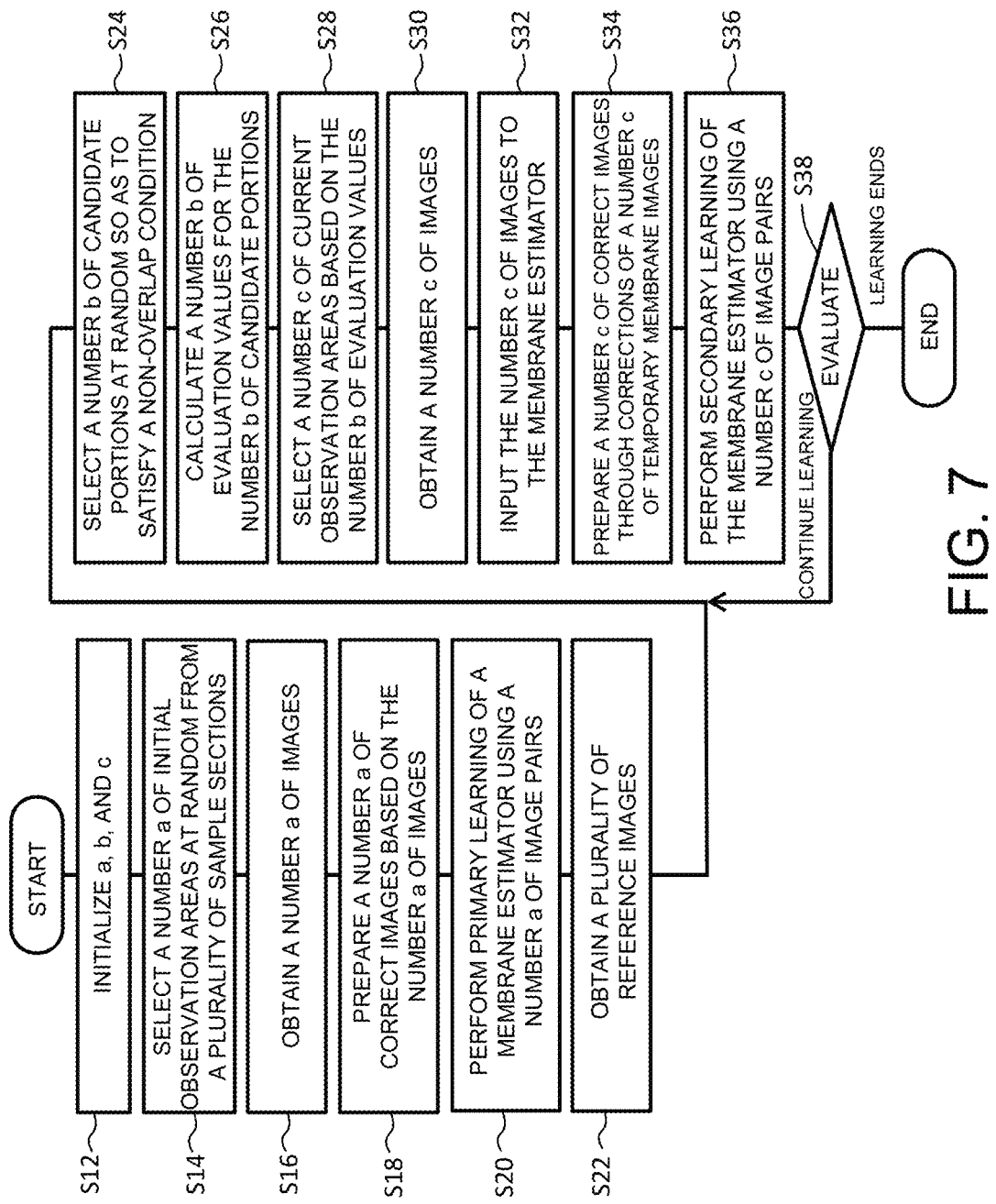
FIG. 7 is a flowchart illustrating a machine learning method according to an embodiment.

FIG. 7 is a flowchart illustrating a machine learning method according to an embodiment. This machine learning method includes a primary learning process (S12 to S20) and a secondary learning process (S24 to S38).

In S12, coefficients a, b, and c are initialized. The coefficient a is a coefficient that sets the count of images that are to be obtained in the primary learning process. The coefficient b is a coefficient that sets the count of candidate areas that are to be set in the secondary learning process. The coefficient c is a coefficient that sets the count of candidate areas that are to be selected as current observation areas from a number b of candidate areas in the secondary learning process. Each of the coefficients a, b, and c is an integer of 1 or greater, where the relationship b>c holds.

In S14, a number a of initial observation areas are selected at random from a plurality of sample sections. A number a of initial observation areas may be selected artificially by a user. In S16, the number a of initial observation areas are sequentially observed under the control of the SEM to thereby obtain a number a of primary learning-purpose images (high magnification images). In S18, a number a of correct images are prepared based on, for example, manual corrections performed on the number a of images.

In S20, a number a of image pairs are input to a membrane estimator that has yet to be subjected to learning, and primary learning (initial learning) of the membrane estimator is executed. The number a of image pairs consist of the number a of images obtained in S16 and the number a of correct images prepared in S18.

In S22, a plurality of sample sections are observed at a low magnification to thereby obtain a plurality of reference images (reference image group). A plurality of reference images may be obtained by observing sample sections either overall or nearly overall at a freely chosen magnification. By obtaining a plurality of low magnification images, typically, the total data amount can be reduced, and the calculation time can be shortened.

Subsequently, the secondary learning process is executed. In S24, a number b of candidate portions are set for the reference image group. The number b of candidate portions, which correspond to a number b of candidate areas that can be ideated on a plurality of sample sections, represents the substance of them. In an embodiment, a number b of candidate portions is set at random. A number b of candidate portions may be set by a different method. In terms of providing diversity, portions that are identical to a plurality of already observed portions that constitute an already observed portion set are excluded from potential portions that can be a number b of candidate portions. In other words, a number b of candidate portions are selected so as to satisfy a non-overlap condition. In that case, whether or not the non-overlap condition is satisfied may be determined based on the degree of overlap.

In S26, a number b of evaluation values are calculated for the number b of candidate portions. In this process, for each of the candidate portions, a plurality of similarities are calculated between the candidate portion and a plurality of already observed portions, and an evaluation value is calculated based on the plurality of similarities. Similarities may be calculated by correlation operation, vector norm operation, or another method. An evaluation value is, for example, a sum or an average value of a plurality of similarities. In S28, a number c of evaluation values corresponding to lower similarities as considered comprehensively (a number c of evaluation values including the lowest evaluation value) are identified from the number b of evaluation values, and a number c of candidate areas are identified from a number c of candidate portions corresponding to the identified evaluation values. The number c of candidate areas are selected as a number c of current observation areas. In S30, the number c of current observation areas are observed at a high magnification. A number c of secondary learning-purpose images are obtained in this manner. Examples of methods of obtaining a plurality of learning-purpose images in the secondary learning process include a first learning-purpose image obtaining method and a second learning-purpose image obtaining method. These methods will be described in detail later with reference to FIGS. 8 to 11.

In S32, the number c of images obtained at S30 are sequentially input to the membrane estimator. In response, a number c of membrane likelihood maps are sequentially output from the membrane estimator. A number c of temporary membrane images are generated based on these membrane likelihood maps. In S34, a number c of correct images are prepared through corrections of the number c of temporary membrane images. In S36, a number c of image pairs that are composed of the number c of images obtained in S30 and their corresponding number c of correct images are input to the membrane estimator, so that secondary learning of the membrane estimator is executed. When, in S38, it is determined that the estimation accuracy of the membrane estimator has yet to reach a certain value (when it is determined that learning should be continued), S24 and subsequent steps are repeatedly executed. When, in S38, it is determined that learning should end, the present processing ends.

In the above-described machine learning method, because, to increase diversity in the learning-purpose image set, a number c of current observation areas are determined in the secondary learning process, the quality of learning of the membrane estimator is enhanced.

Figure 8:
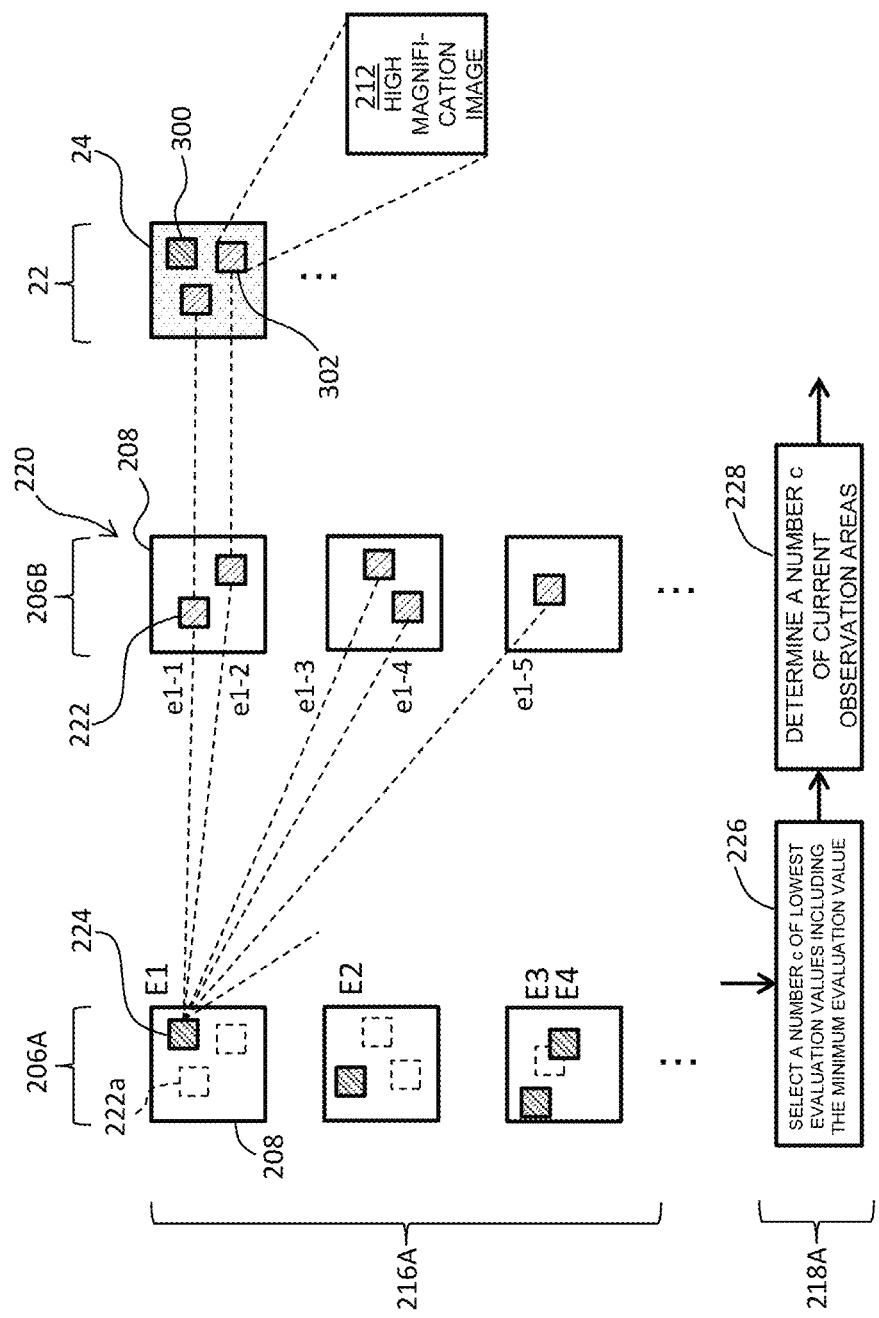
FIG. 8 illustrates a first learning-purpose image obtaining method.

FIG. 8 illustrates a first learning-purpose image obtaining method. In an embodiment, this first learning-purpose image obtaining method is executed in the secondary learning process. This learning-purpose image obtaining method may also be executed in, for example, the primary learning process.

Referring to FIG. 8, reference numeral 216A in the upper left represents processing that is executed by the evaluation value calculation unit. Reference numeral 218A in the lower left represents processing that is executed by the observation area determiner. In FIG. 8, the same reference image group is expressed as a reference image group 206A (see the left side in the figure) and a reference image group 206B (see the center in the figure) for simplicity and ease of description. A sample section group 22 is illustrated in the right side in the figure.

A plurality of candidate portions 224 are determined for the reference image group 206A. The plurality of candidate portions 224 represent the substance of a plurality of candidate areas 300 that are ideated in the sample section group 22. For example, the plurality of candidate portions 224 are selected at random from the reference image group 206A. In this process, selection processing is executed so as to prevent any of already observed portions 222, which will be described below, from being selected as a candidate portion 224 or, in other words, so as to satisfy the non-overlap condition. The non-overlap condition is a condition for preventing an already observed area 302 from being redundantly observed as a current observation area as described above. Diversity in a learning-purpose image set can be ensured in this manner. In the reference image group 206A, a plurality of already observed portions are depicted by broken lines (see reference numeral 222a).

The reference image group 206B includes a plurality of already observed portions 222. They constitute an already observed portion set 220. The plurality of already observed portions 222 represent the substance of a plurality of the already observed areas 302 in the sample section group 22. As described above, a plurality of reference images 208 are obtained through low magnification observation of the plurality of sample sections 24, and, for example, each of the reference images 208 represents a sample section 24 either overall or nearly overall.

The sample section group 22 for the learning purpose is composed of the plurality of sample sections 24. As described above, the plurality of sample sections 24 include the plurality of already observed areas 302, and a plurality of candidate areas 300 can be ideated in the plurality of sample sections 24. The plurality of already observed areas 302 have been observed at a high magnification to thereby obtain a plurality of high magnification images (learning-purpose images) 212.

To calculate an evaluation value for each of the candidate portions 224, a plurality of similarities are calculated between the candidate portion 224 and the plurality of already observed portions 222 that constitute the already observed portion set 220. An evaluation value is calculated from the plurality of similarities. An evaluation value is determined as, for example, a sum, an average value, or another value (such as a minimum value, a maximum value, or a center of gravity value) of a plurality of similarities. The evaluation value is a similarity evaluation value for obtaining a total evaluation of magnitude of similarity.

In a specific example illustrated in FIG. 8, a plurality of similarities that are individually calculated between a first candidate portion 224 and the plurality of already observed portions 222 are denoted as e1-1, e1-2, e1-3, e1-4, e1-5, . . . . An evaluation value E1 is calculated from these similarities. This process is executed for each of the candidate portions 224, and as a result, a plurality of evaluation values E1, E2, E3, . . . are calculated for the plurality of candidate portions 224. When, for example, the count of candidate portions 224 is m, and the count of already observed portions 222 is n, a number n of similarities are calculated for each of the candidate portions 224, and based on these similarities, a number m of evaluation values are calculated for a number m of candidate portions 224.

As illustrated by reference numeral 226, the observation area determiner selects, from the plurality of evaluation values calculated as described above, a number c of lowest evaluation values including the minimum value (corresponding to the lowest similarity). Subsequently, as illustrated by reference numeral 228, the observation area determiner determines a number c of candidate areas corresponding to the number c of selected evaluation values as a number c of current observation areas. Here, c is any integer of 1 or greater. The above-described processing is repeatedly executed up until sufficient learning results are obtained.

Because the above-described first learning-purpose image obtaining method can determine one or a plurality of current observation areas based on an already observed area set, diversity in a learning-purpose image set can be increased, achieving an increase in learning efficiency of an estimator.

A second learning-purpose image obtaining method will next be described with reference to FIGS. 9 to 11. In an embodiment, the second learning-purpose image obtaining method is executed in the secondary learning process. The second learning-purpose image obtaining method may also be executed in, for example, a subsequent learning process.

Figure 9:
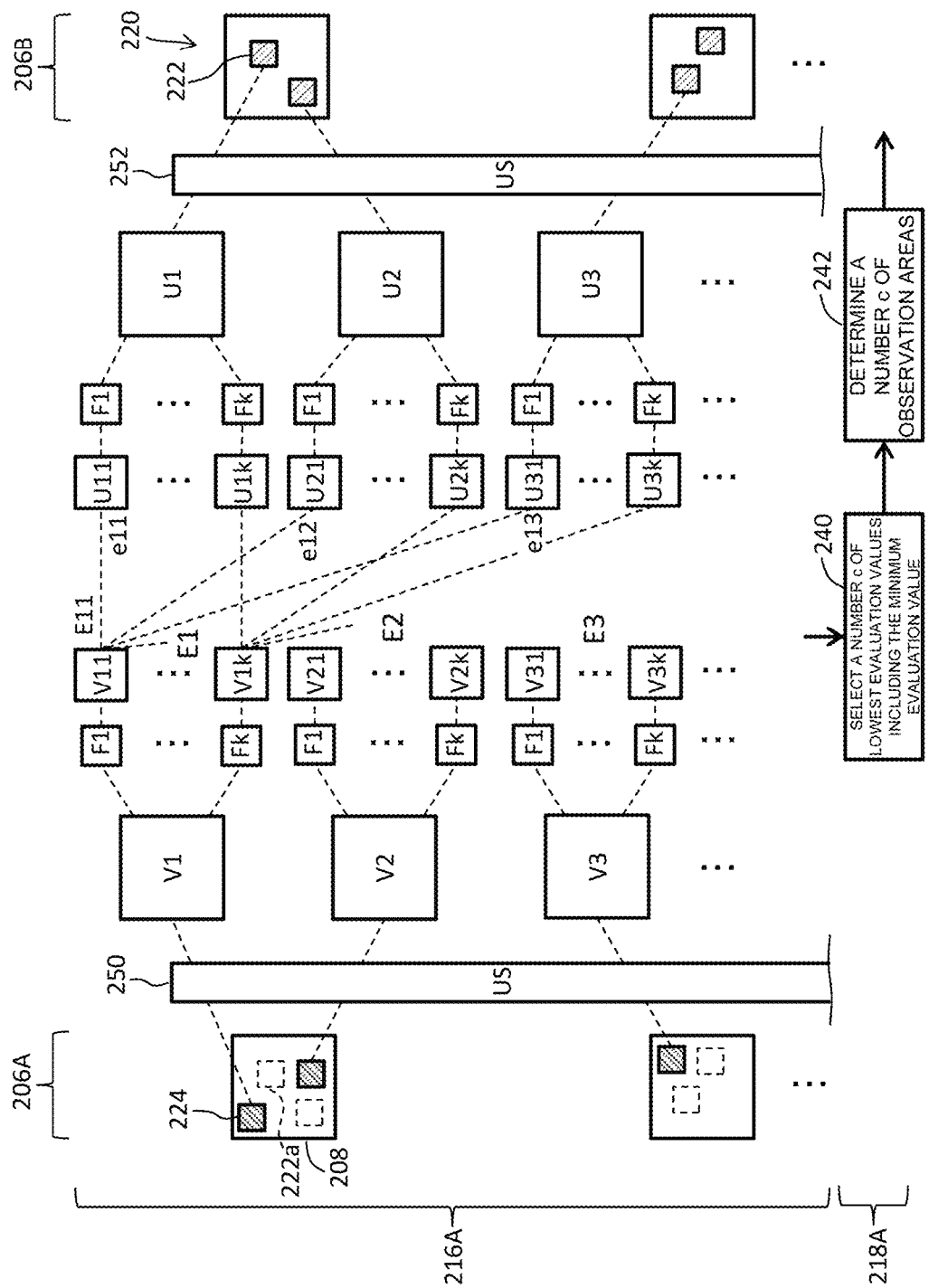
FIG. 9 illustrates a second learning-purpose image obtaining method.

Referring to FIG. 9, reference numeral 216A in the upper left represents processing that is executed by the evaluation value calculation unit, and reference numeral 218A in the lower left represents processing that is executed by the observation area determiner. In FIG. 9, similarly as in FIG. 8 described above, the same reference image group is expressed as a reference image group 206A (see the left side in the figure) and a reference image group 206B (see the right side in the figure), for simplicity and ease of description. In FIG. 9, the sample section group is not illustrated. It should be noted that in FIG. 9, components similar to the components illustrated in FIG. 8 are assigned the same reference numerals.

A plurality of candidate portions 224 are determined for the reference image group 206A. For example, the plurality of candidate portions 224 are selected at random from the reference image group 206A. In this process, selection processing is executed so as to satisfy the above-described non-overlap condition. In the reference image group 206A, a plurality of already observed portions are depicted by broken lines (see reference numeral 222a). The reference image group 206B includes a plurality of already observed portions 222. They constitute an already observed portion set 220.

A number k of filters F1 to F$k$ that constitute a filter row are a plurality of convolution filters that are taken out from a membrane estimator that is composed of a CNN. FIG. 9 illustrates two filter rows, one in the center toward the right side and the other in the center toward the left side, for simplicity and ease of description. They are identical in substance. In the membrane estimator, each of the filters has a size that is smaller than the size of a target image and extracts a characteristic amount from the target image through convolution operation. In an embodiment, a number k of filters F1 to F$k$ that function in parallel are taken out and used in evaluation value calculation. All filters of the membrane estimator may be used in evaluation value calculation, and some filters of the membrane estimator may be used. A certain filter of the membrane estimator may also be used. To calculate similarities while taking into consideration processing in the membrane estimator, it is generally preferable that as many filters of the membrane estimator as possible are used.

In FIG. 9, a US 250 is a module that performs upsampling on the plurality of candidate portions 224, and a US 252 is a module that performs upsampling on the plurality of already observed portions 222. The US 250 and the US 252 may be composed of a single module. Upsampling is processing that converts a low magnification image into an image that is equivalent to a high magnification image (image that is input to the membrane estimator). An image that has been subjected to the conversion has the same number of pixels and apparent magnification as the image that is input to the membrane estimator. In FIG. 9, a plurality of candidate portions that have been subjected to the upsampling are expressed as V1, V2, V3, . . . .

Subsequently, the filters F1 to F$k$ are applied to each of the plurality of candidate portions V1, V2, V3, . . . that have been subjected to the upsampling to thereby generate a plurality of candidate portions V11, . . . , V1$k$, V21, . . . , V2$k$, V31, . . . , V3$k$, . . . that have been subjected to the upsampling and the filter processing.

On the other hand, the US 252 applies upsampling to the plurality of already observed portions 222 to thereby generate a plurality of already observed portions U1, U2, U3, . . . that have been subjected to the upsampling. Subsequently, the filters F1 to F$k$ are applied to each of the plurality of already observed portions U1, U2, U3, . . . that have been subjected to the upsampling to thereby generate a plurality of already observed portions U11, . . . , U1$k$, U21, . . . , U2$k$, U31, . . . , U3$k$, . . . that have been subjected to the upsampling and the filter processing.

In the process of evaluation value calculation, a plurality of individual similarities are calculated between a plurality of candidate portions V11, . . . , V1$k$, V21, . . . , V2$k$, V31, . . . , V3$k$, . . . that have been subjected to the upsampling and the filter processing and a plurality of already observed portions U11, . . . , U1$k$, U21, . . . , U2$k$, U31, . . . , U3$k$, . . . that have been subjected to the upsampling and the filter processing. In this process, individual similarities are calculated for all combinations (each being a combination of two portions) to each of which the same filter processing has been applied.

For example, a plurality of individual evaluation values e11, e12, e13, . . . are calculated between the first candidate portion V11 and a plurality of already observed portions U11, U21, U31, . . . to which the same filter processing has been applied. Similarly, a plurality of individual similarities are calculated between a second candidate portion and a plurality of already observed portions to which the same filter processing has been applied. In the end, individual similarities are calculated in this manner for all combinations to each of which the same filter processing has been applied. Evaluation values E1, E2, E3, . . . are each calculated for a corresponding one of the candidate portions 224 based on a plurality of individual similarities that are calculated for the candidate portion 224, as, for example, a sum or an average value of the plurality of individual similarities. As in the first learning-purpose image obtaining method, each of the evaluation values E1, E2, E3, . . . represents magnitude of similarity that each of the candidate areas has relative to the already observed area set.

In summary, when the count of candidate portions 224 is m, the count of already observed portions 222 is n, and the count of filters is k, then, for each of the candidate portions 224, a number k×n of individual similarities are calculated, and an evaluation value is calculated as, for example, a sum of the number k×n of individual similarities. In other words, a number m of evaluation values are calculated for a number m of candidate portions 224. Evaluation value calculation may be performed in two stages. For example, for each of the candidate portions V11, . . . , V1k, V21, . . . , V2k, V31, . . . , V3k, . . . that have been subjected to the upsampling and the filter processing, an intermediate evaluation value (see, for example, E11) may be determined based on a number n of individual similarities, and subsequently, for each of the candidate portions 224, the evaluation value E1 may be determined from a number k of intermediate evaluation values. In this case as well, a number m of evaluation values are determined for a number in of candidate portions 224.

As illustrated by reference numeral 240, the observation area determiner selects, from the plurality of evaluation values calculated as described above, a number c of lowest evaluation values including the minimum value (corresponding to the lowest similarity). Subsequently, as illustrated by reference numeral 242, the observation area determiner determines a number c of candidate areas corresponding to the number c of selected evaluation values as a number c of current observation areas. The above-described processing is repeatedly executed up until sufficient learning results are obtained.

Because, as in the first learning-purpose image obtaining method, the above-described second learning-purpose image obtaining method can determine one or a plurality of current observation areas based on an already observed area set, diversity in a learning-purpose image set is increased, thereby achieving an increase in learning efficiency. Also, an evaluation value can be calculated while taking into consideration all, some, or one of the characteristics of the membrane estimator.

Figure 10:
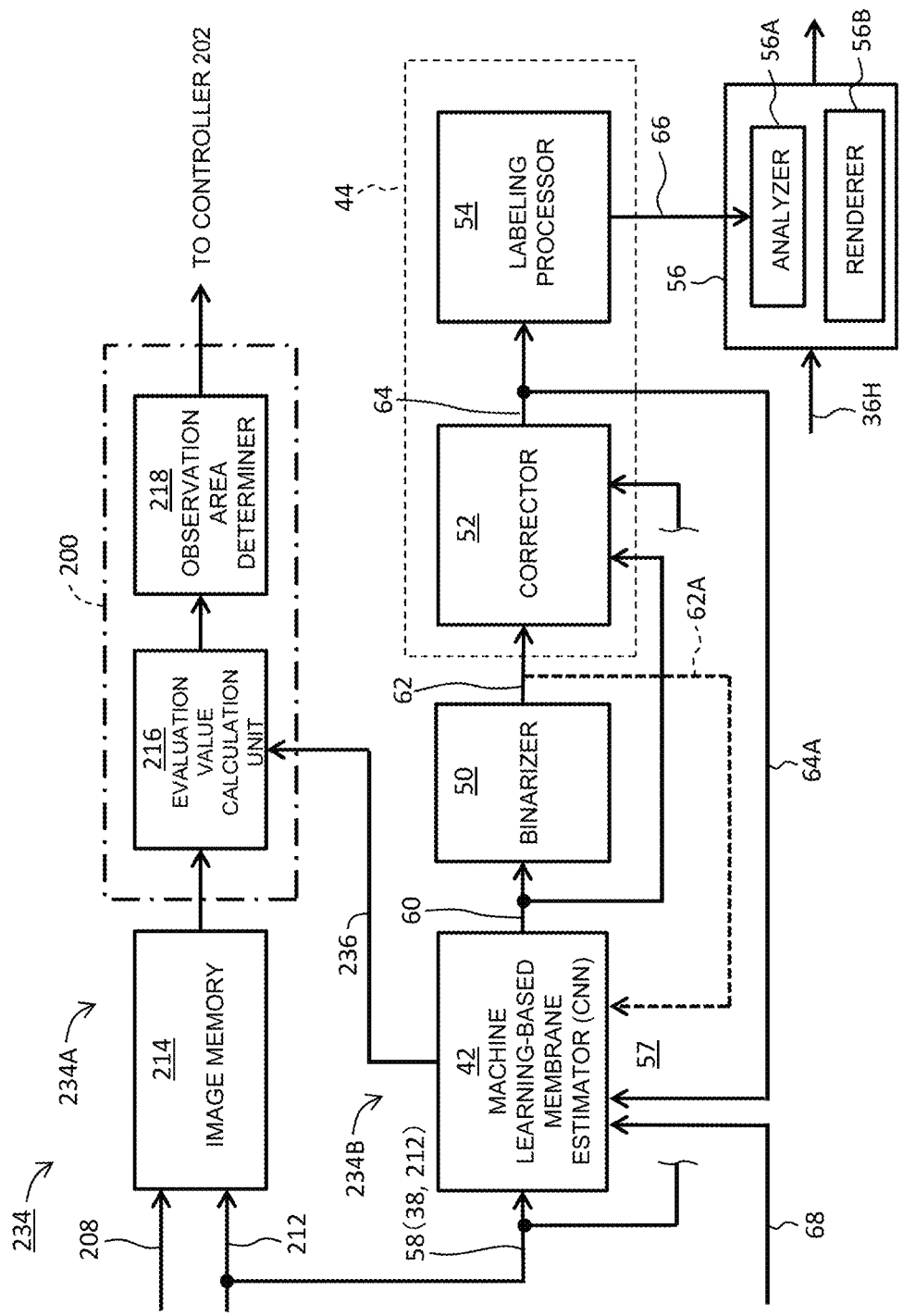
FIG. 10 is a block diagram illustrating a second example structure of the main unit for performing the second learning-purpose image obtaining method.

To perform the second learning-purpose image obtaining method, a structure illustrated in, for example, FIG. 10 is used. FIG. 10 illustrates a second example structure of the main unit. It should be noted that components similar to the components illustrated in FIG. 2 are assigned the same reference numerals, and their descriptions are not repeated here.

Referring to FIG. 10, a main unit 234 is composed of a learning control subsystem 234A and an image processing subsystem 234B. A filter row (plurality of convolution filters) 236 included in the membrane estimator 42 is taken out and is transmitted to the evaluation value calculation unit 216. Through the processing illustrated in FIG. 9, the evaluation value calculation unit 216 calculates an evaluation value for each of a plurality of candidate areas using the filter row 236.

Figure 11:
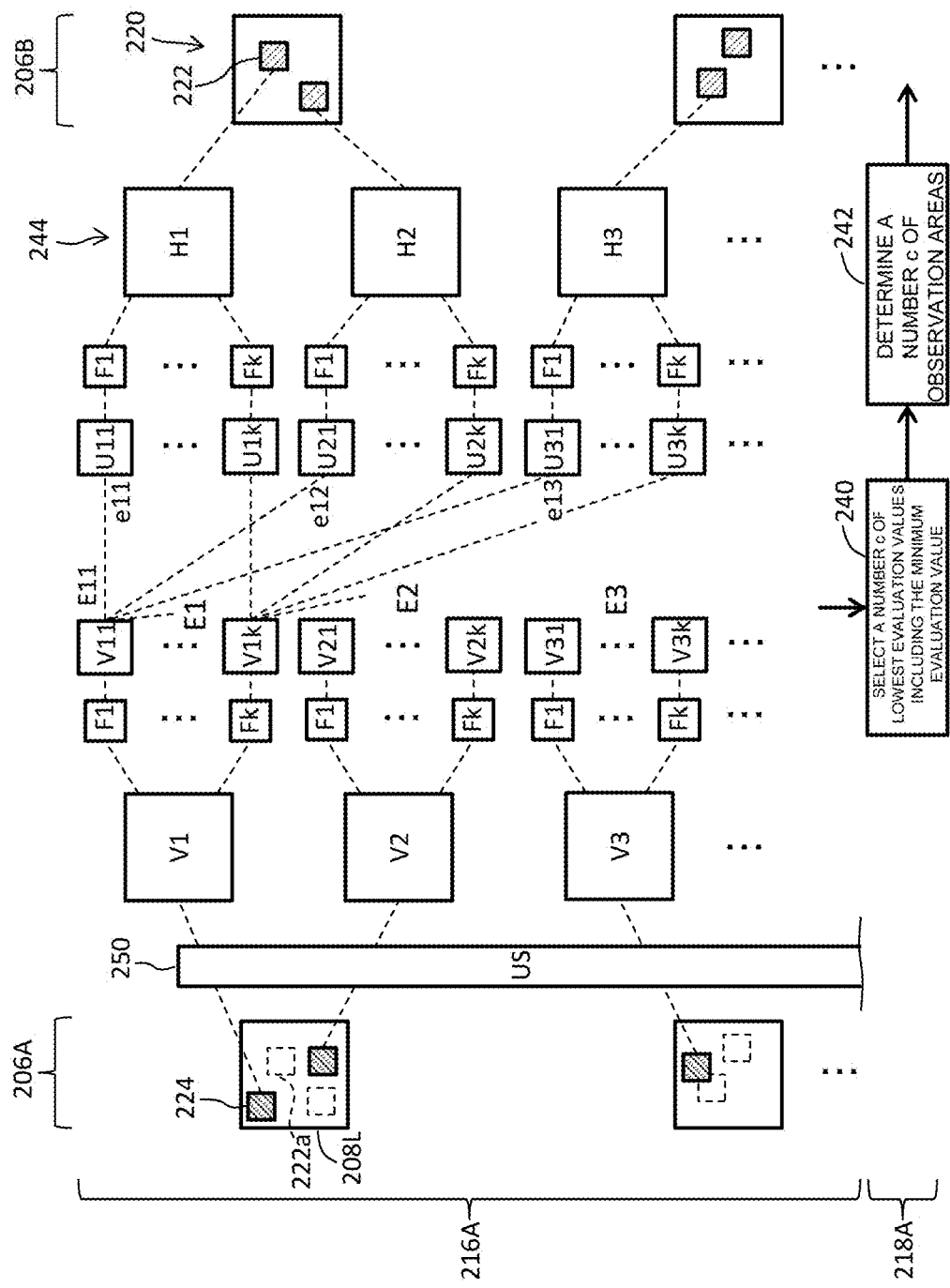
FIG. 11 illustrates a modification example of the second learning-purpose image obtaining method.

FIG. 11 illustrates a modification example of the second learning-purpose image obtaining method. Components similar to the components illustrated in FIG. 9 are assigned the same reference numerals, and their descriptions are not repeated here. In FIG. 11, the US 252 illustrated in FIG. 9 is removed. In FIG. 11, instead of the plurality of already observed portions (high density images) U1, U2, U3, . . . that have been subjected to the upsampling, a plurality of learning-purpose images (high density images) H1, H2, H3, . . . obtained from a plurality of already observed areas are used. Filter processing is applied to each of the plurality of learning-purpose images H1, H2, H3, . . . . As a result, a plurality of already observed portions U11, . . . , U1k, U21, . . . , U2k, U31, . . . , U3k, . . . that have been subjected to the filter processing are generated based on the plurality of learning-purpose images. A plurality of evaluation values E1, E2, E3, . . . are calculated by the same method as that illustrated in FIG. 9.

In this modification example as well, because one or a plurality of current observation areas can be determined based on past observation results, learning efficiency of the membrane estimator is increased. Also, an evaluation value can be calculated while taking into consideration all, some, or one of the characteristics of the membrane estimator.

The invention claimed is:

1. A biological tissue image processing system, comprising:
   a machine learning-based estimator configured to apply processing to an image obtained through observation of biological tissue using a microscope, the processing estimating a target component included in the biological tissue;
   a determiner configured to determine a current observation area in the biological tissue in a machine learning process of the estimator; and
   a controller configured to control operation of the microscope to cause the current observation area to be observed in the machine learning process of the estimator,
   wherein the determiner comprises,
   a similarity calculator configured to calculate, for each of candidate areas in the biological tissue, a plurality of similarities between the candidate area and a plurality of already observed areas in the biological tissue,
   an evaluation value calculator configured to calculate, for each of the candidate areas in the biological tissue, an evaluation value based on the plurality of similarities, wherein the evaluation value represents the degree to which the candidate area is similar to an already observed area set which consists of the plurality of already observed areas, and
   a selector configured to select, from the plurality of candidate areas in the biological tissue, a particular candidate area as the current observation area based on a plurality of evaluation values for the plurality of candidate areas in the biological tissue.

2. The biological tissue image processing system according to claim 1,
   wherein the image that is input to the estimator is an image obtained through high magnification observation of the biological tissue,
   wherein a reference image group consisting of one or a plurality of reference images is obtained through low magnification observation of the biological tissue, and wherein the similarity calculator is configured to calculate the plurality of similarities based on a candidate portion corresponding to the candidate area in the reference image group and a plurality of already observed portions corresponding to the plurality of already observed areas in the reference image group.

3. The biological tissue image processing system according to claim 2, wherein the similarity calculator includes:
a first upsampling processor configured to apply upsampling to the candidate portion;
a second upsampling processor configured to apply upsampling to the plurality of already observed portions;
a first filter processor configured to apply, to the candidate portion that has been subjected to the upsampling, at least one convolution filter that is included in the estimator;
a second filter processor configured to apply, to the plurality of already observed portions that have been subjected to the upsampling, the at least one convolution filter that is included in the estimator; and
a calculator configured to calculate the plurality of similarities based on the candidate portion to which the upsampling and the at least one convolution filter have been applied and the plurality of already observed portions to which the upsampling and the at least one convolution filter have been applied.

4. The biological tissue image processing system according to claim 2, wherein the similarity calculator includes:
an upsampling processor configured to apply upsampling to the candidate portion;
a first filter processor configured to apply, to the candidate portion that has been subjected to the upsampling, at least one convolution filter that is included in the estimator;
a second filter processor configured to apply, to a plurality of high magnification images corresponding to the plurality of already observed portions, the at least one convolution filter that is included in the estimator; and
a calculator configured to calculate the plurality of similarities based on the candidate portion to which the upsampling and the at least one convolution filter have been applied and the plurality of high magnification images to which the at least one convolution filter has been applied.

5. The biological tissue image processing system according to claim 2,
wherein the plurality of reference images are obtained through low magnification observation of a plurality of biological tissue sections corresponding to a plurality of depths in the biological tissue.

6. The biological tissue image processing system according to claim 5,
wherein the microscope includes a movement mechanism configured to move a substrate relative to an observation optical axis, the substrate having the plurality of biological tissue sections placed thereon, and
wherein the controller is configured to control the movement mechanism to cause the current observation area to be observed at a high magnification.

7. A biological tissue image processing system, comprising:
at least one processor configured to apply processing to an image obtained through observation of biological tissue using a microscope, the processing estimating a target component included in the biological tissue;
at least one processor configured to determine a current observation area in the biological tissue in a machine learning process; and
a controller configured to control operation of the microscope to cause the current observation area to be observed in the machine learning process,
wherein the at least one processor is configured to:
calculate, for each of candidate areas in the biological tissue, a plurality of similarities between the candidate area and a plurality of already observed areas in the biological tissue,
calculate, for each of the candidate areas in the biological tissue, an evaluation value based on the plurality of similarities, wherein the evaluation value represents the degree to which the candidate area is similar to an already observed area set which consists of the plurality of already observed areas, and
select, from the plurality of candidate areas in the biological tissue, a particular candidate area as the current observation area based on a plurality of evaluation values for the plurality of candidate areas in the biological tissue.

* * * * *